US006602071B1

(12) United States Patent
Ellion et al.

(10) Patent No.: US 6,602,071 B1

(45) Date of Patent: Aug. 5, 2003

(54) HAND-HELD SELF-CONTAINED CLEANING SYSTEM

(76) Inventors: M. Edmund Ellion, 3660 Woodstock Rd., Santa Ynez, CA (US) 93460; Mark J. Shultz, 678 Alamo Pintado Rd., Solvang, CA (US) 93463

( * ) Notice: Subject to any disclaimer, the term of this patent is extended or adjusted under 35 U.S.C. 154(b) by 0 days.

(21) Appl. No.: 09/681,122

(22) Filed: Jan. 13, 2001

(51) Int. Cl.[7] ........................ A61G 17/02; A61C 17/06; A61C 15/00; A61H 13/00; A61M 35/00

(52) U.S. Cl. ........................... 433/80; 433/91; 132/322; 601/162; 604/294

(58) Field of Search ............................. 433/80, 91, 95, 433/89; 601/162; 222/95, 324, 325, 341, 385, 389; 132/112, 116, 322; 604/294; 417/256, 257, 259, 534, 535, 536, 538; 137/596.18, 565.26; 15/345, 346, 341, 344

(56) References Cited

U.S. PATENT DOCUMENTS

| | | | | | |
|---|---|---|---|---|---|
| 984,098 | A | * | 2/1911 | Lundin | 15/341 |
| 3,164,153 | A | * | 1/1965 | Zorzi | 433/80 |
| 3,624,907 | A | * | 12/1971 | Brass et al. | 433/80 |
| 4,221,548 | A | * | 9/1980 | Child | 417/534 |
| 4,393,536 | A | * | 7/1983 | Tapp | 15/346 |
| 4,571,849 | A | * | 2/1986 | Gardner et al. | 15/346 |
| 5,076,769 | A | * | 12/1991 | Shao | 417/534 |
| 5,094,256 | A | * | 3/1992 | Barth | 132/322 |
| 5,145,367 | A | * | 9/1992 | Kasten | 433/80 |
| 5,201,726 | A | * | 4/1993 | Kirkham | 604/294 |
| 5,407,424 | A | * | 4/1995 | LaFontaine et al. | 417/534 |
| 5,553,347 | A | * | 9/1996 | Inoue et al. | 15/346 |
| 5,570,709 | A | * | 11/1996 | Haddad et al. | 132/322 |
| 5,573,398 | A | * | 11/1996 | Towle et al. | 433/80 |
| 5,746,595 | A | * | 5/1998 | Ford | 433/80 |
| 5,762,606 | A | * | 6/1998 | Minnich | 604/294 |
| 5,817,955 | A | * | 10/1998 | Gherson et al. | 417/535 |
| 6,030,215 | A | | 2/2000 | Ellion et al. | |
| 6,083,003 | A | * | 7/2000 | Kwasnik et al. | 433/91 |
| 6,108,863 | A | * | 8/2000 | Lin | 15/346 |
| 6,155,824 | A | * | 12/2000 | Kamen et al. | 433/80 |
| 6,217,328 | B1 | * | 4/2001 | Oliver | 433/80 |
| 6,267,752 | B1 | * | 7/2001 | Svetliza | 604/294 |
| 6,315,556 | B1 | * | 11/2001 | Stewart | 433/80 |

* cited by examiner

*Primary Examiner*—Todd E. Manahan
(74) *Attorney, Agent, or Firm*—Hugh Gortler

(57) ABSTRACT

A handheld cleaning device includes a cleaning section having discharge and suction ports; and a pump for causing fluid to be discharged through the discharge port of the cleaning section and for simultaneously creating suction at the suction port of the cleaning section.

18 Claims, 9 Drawing Sheets

FIG. 5b
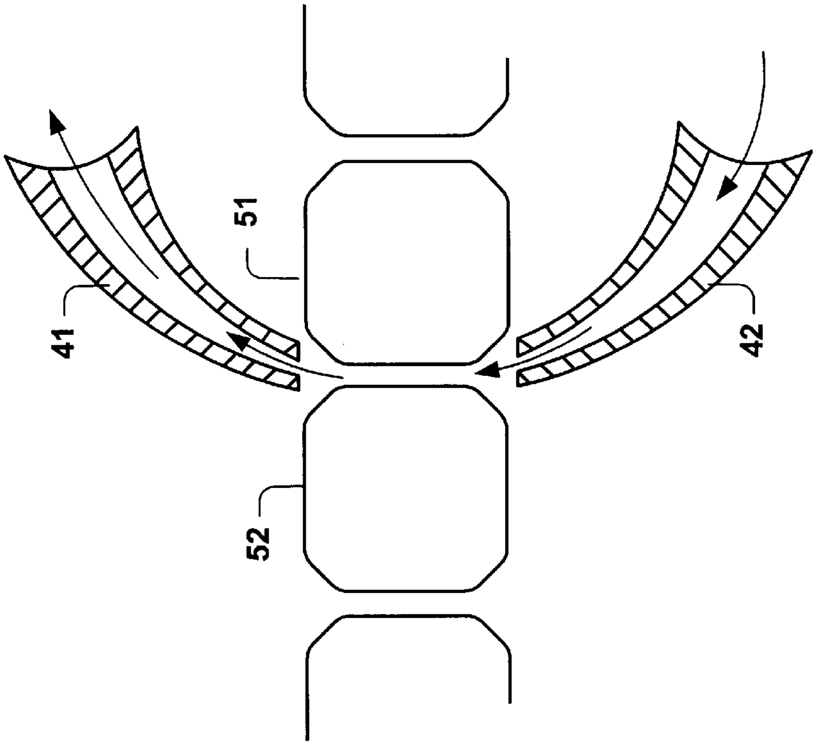
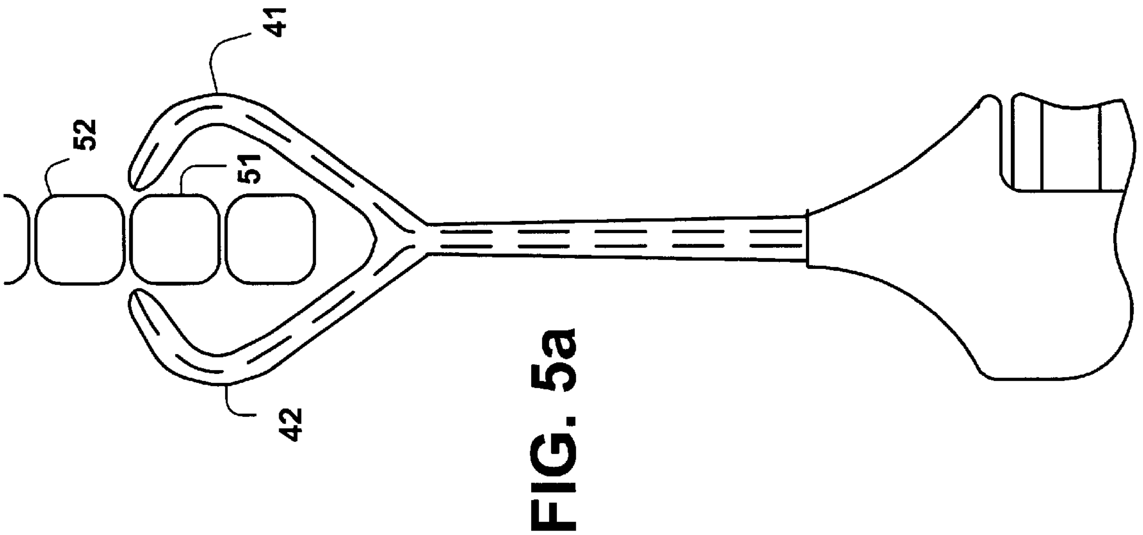
FIG. 5a

FIG. 11b
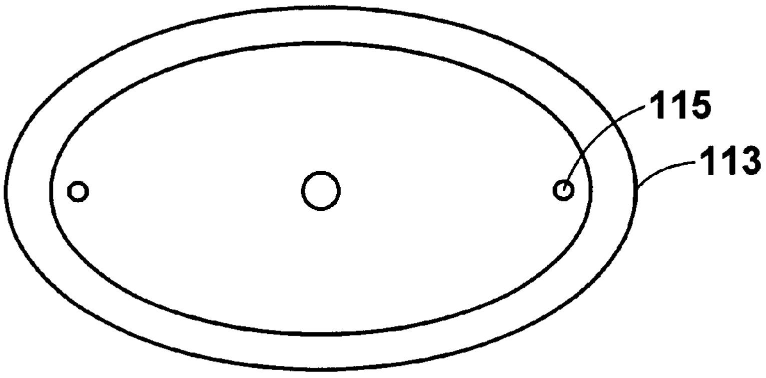
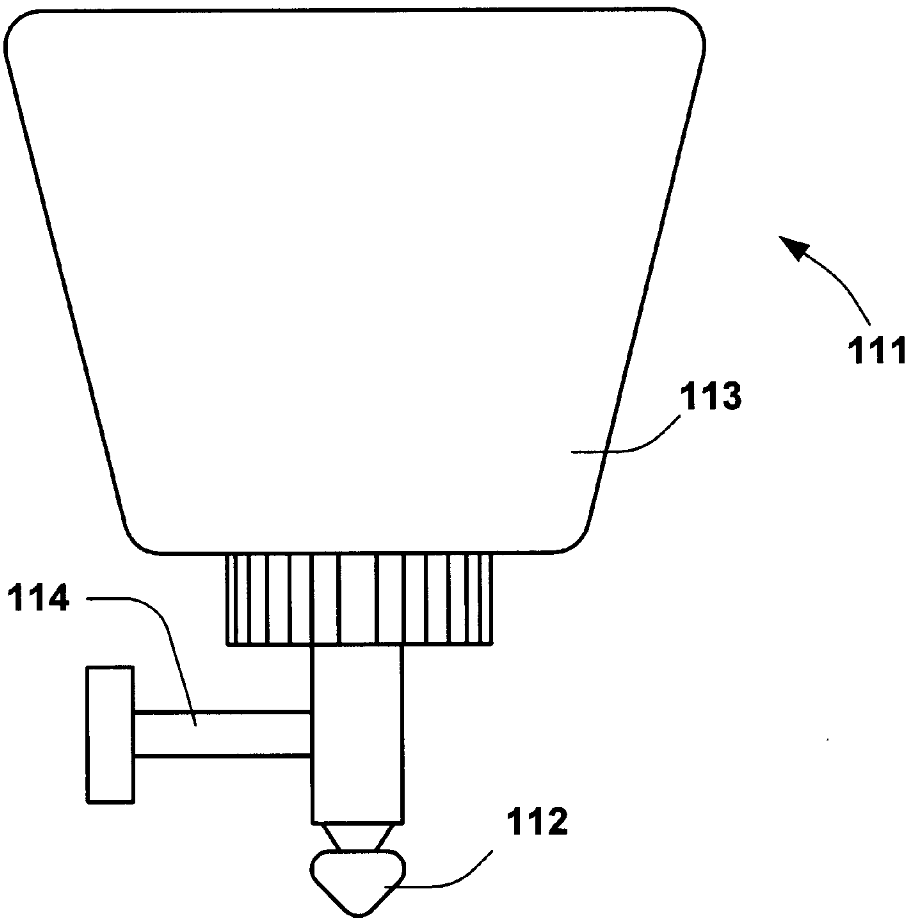
FIG. 11a

HAND-HELD SELF-CONTAINED CLEANING SYSTEM

BACKGROUND OF INVENTION

The invention relates to a handheld irrigation device including a hand-operated pump. The invention also relates to attachments for the hand-held irrigation device.

Over 90 percent of the adult population is infected with some form of periodontal disease. Most periodontal disease begins in the interproximal area of the mouth between the teeth. This degradation results from bacteria that are nourished from food debris that are not removed from the gum area. Anaerobic bacterial activity in this ecological region of the gingival sulcus is the major cause of periodontal disease. Therefore, removing contaminants from the gingival sulcus is highly desirable. Brushing does not always effectively remove contaminants, and flossing is not completely effective either.

There is a need for an inexpensive, compact, hand-held, portable finger-operated oral cleaning system that is completely self-contained, that can lavage between teeth and around the gum line with a dental fluid, and that can also withdraw the fluid to facilitate debridement of food particles and bacterial plague.

There is also a need for the system to provide an adjustable fluid stream pressure that remains relatively constant during the operation.

There is also a need for the system to provide an adjustable volume for each pulse of fluid.

There is also a need for the system to provide an attachment capability for various types of cleaning devices.

SUMMARY OF INVENTION

According to one aspect of the invention, a handheld cleaning device comprises a cleaning section having discharge and suction ports; and a pump for causing fluid to be discharged through the discharge port of the cleaning section and for simultaneously creating suction at the suction port of the cleaning section.

BRIEF DESCRIPTION OF DRAWINGS

FIG. 5*a* is a view of the dual irrigator attachment positioned between two teeth.

FIG. 5*b* is a sectional view of the dual irrigator attachment.

FIGS. 11*a* and 11*b* are illustrations of an eye rinse attachment for the cleaning device.

DETAILED DESCRIPTION

Figure 1:
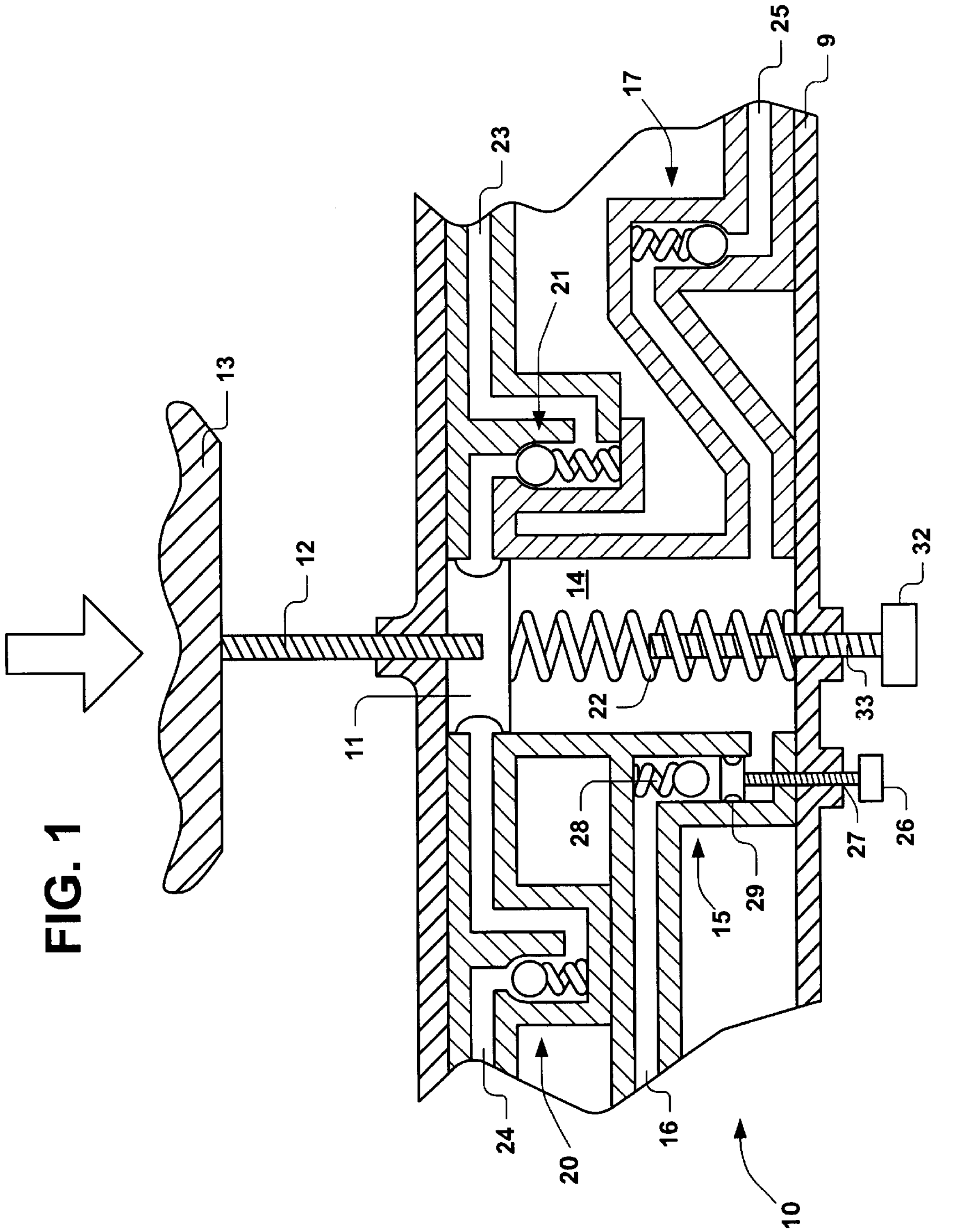
FIG. 1 is a sectional side view of a dual-function hand pump during a first stroke.

FIG. 1 illustrates a two-stroke dual-stroke hand pump 10. A single piston 11 is connected to an actuator rod 12, which is connected to a finger grip 13.

When the finger grip 13 is depressed, the piston 11 is forced into a first chamber 14, causing the pressure therein to increase and force a first valve 15 to open, causing fluid in the first chamber 14 to be expelled through a first conduit 16. At the same time, a second valve 17 is forced to close, preventing the fluid in the first chamber 14 from flowing out of a second conduit 25.

Concurrently, the pressure in a second chamber 19 formed on the opposite side of the piston 11 is caused to decrease, thereby causing a third valve 20 to open and a fourth valve 21 to close. As a result, the second chamber 19 draws fluid from a third conduit 24 but not from a fourth conduit 23.

Figure 2:
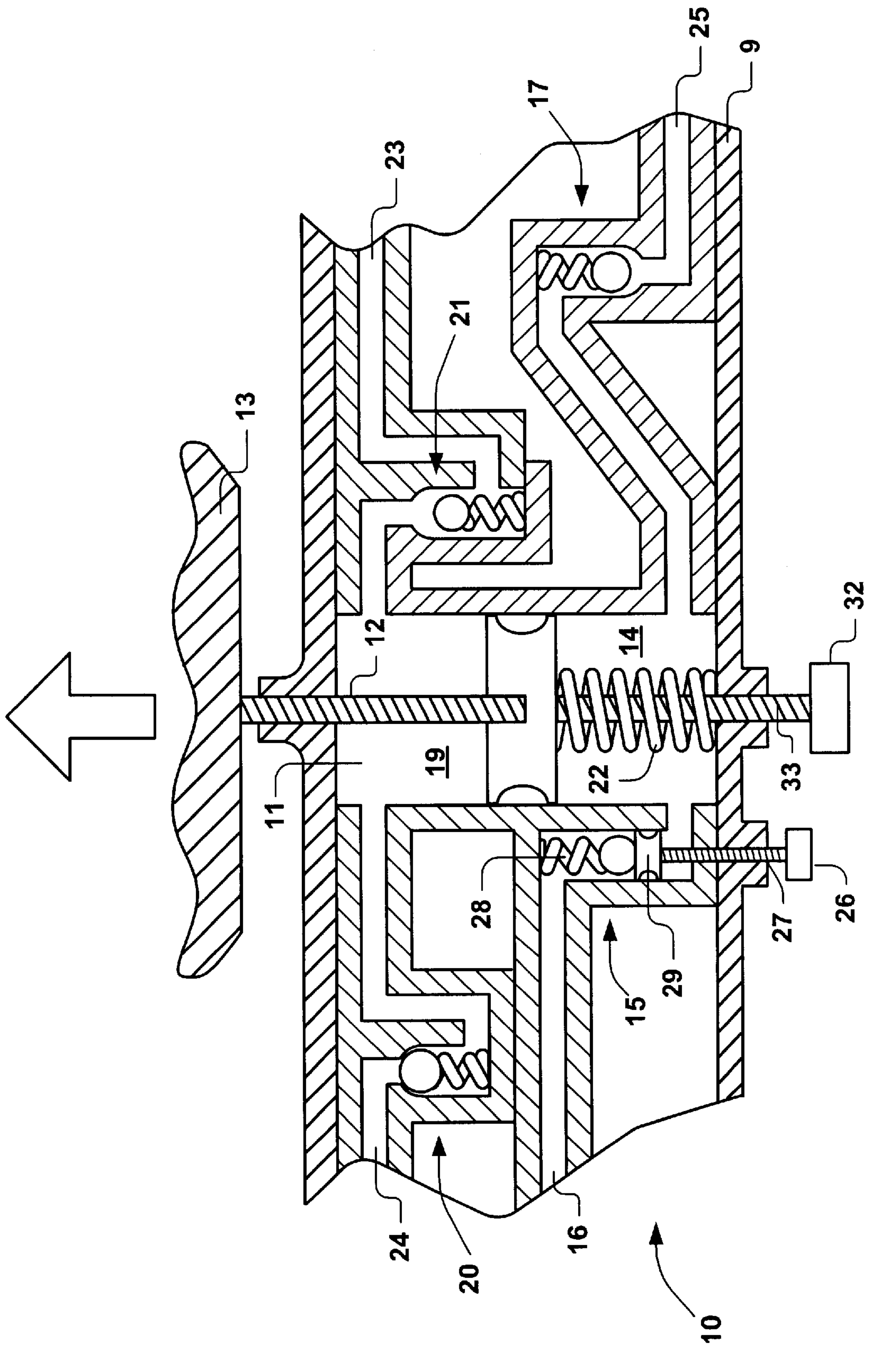
FIG. 2 is a sectional side view of the dual-function hand pump during a second stoke.

Additional reference is made to FIG. 2. When the finger grip 13 is released, the piston 11 is forced to rise by the action of a spring 22. As the pressure in the first chamber 14 decreases, the second valve 17 is forced open and fluid is admitted through the second conduit 25. Concurrently, the first valve 15 is caused to close, thereby preventing fluid from entering the first chamber 14 via the first conduit 16. Simultaneously, the pressure in the second chamber 19 is increased, causing the fourth valve 21 to open and the third valve 20 to close, whereby the fluid in the second chamber 19 is ejected through the fourth conduit 23. During the next two-stroke cycle, this process is repeated.

This single piston pump 10 can provide both a pressurized stream of fluid and vacuum suction simultaneously.

The dual-function pump 10 can control volume and discharge pressure of the fluid discharged from the first conduit 16. A first screw 32 mates with screw threads 33 of the pump's housing 9 to allow axial motion of the screw 32 and thereby limit the downward stroke of the piston 11 Rotating the first screw 32 causes it to enter or leave the first chamber 14 and thereby control the volume of the chambers 14 and 19 (the first screw 32 sets the minimum volume of the first chamber 14 and the maximum volume of the second chamber 19). Thus the first screw 32 controls the volume (amount) of the discharge through the first conduit 16 for each stroke of the pump 10.

Similarly, a second screw 26 mates with a threaded section 27 in the pump housing 9 and can be adjusted to increase or decrease the force of a spring 28 on a valve seat 29 of the first valve 15. The second screw 26 can be adjusted to control the discharge pressure of the fluid that is discharged from the first conduit 16.

Figure 3:
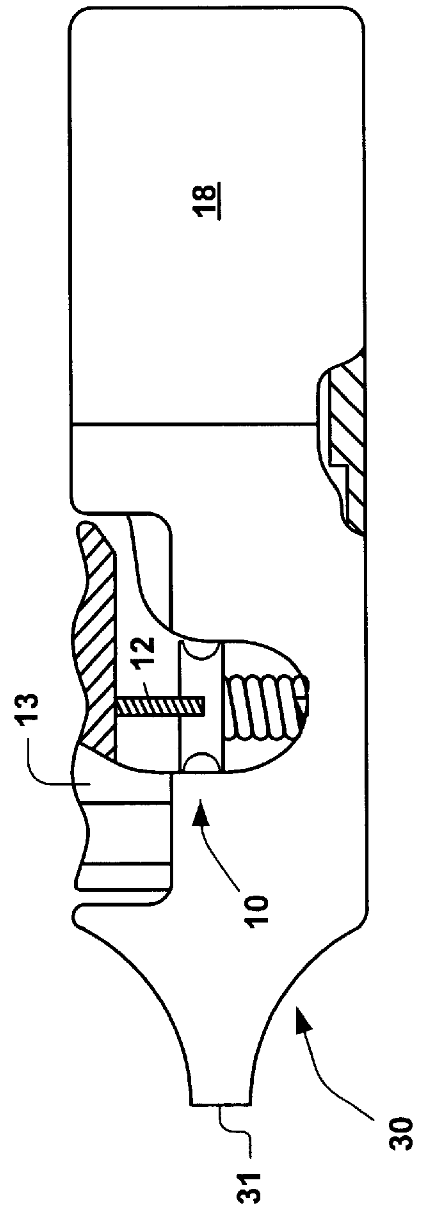
FIG. 3 is a side view of a cleaning device including the dual-function pump.

A hand-held cleaning device 30 illustrated in FIG. 3 includes the pump 10, the actuator rod 12, the finger grip 13, a fluid reservoir section 18 in fluid communication with the second conduit 25, a longitudinally spaced fluid discharge section 31 in fluid communication with the first and third conduits 16 and 24 of the pump 10, and a longitudinally spaced body 34 surrounding the hand pump 10.

Figure 9:
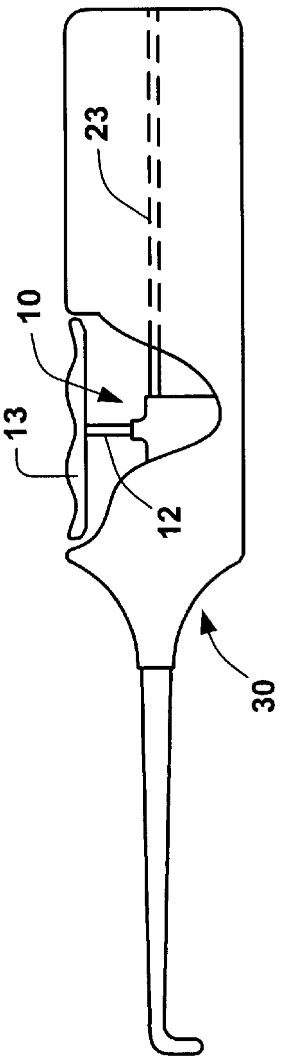
FIG. 9 illustrates a fluid discharge path in the cleaning device.

The fourth conduit 23 may be vented to ambient (see FIG. 9). This allows the fluid in the second chamber 19 to be ejected through the fourth conduit 23 and out of the device 30. For example, the fluid may be ejected into a sink.

Various cleaning attachments may be attached to the discharge section 31 of the device 30. Exemplary attachments are illustrated in FIGS. 4–12*b*.

Figure 4:
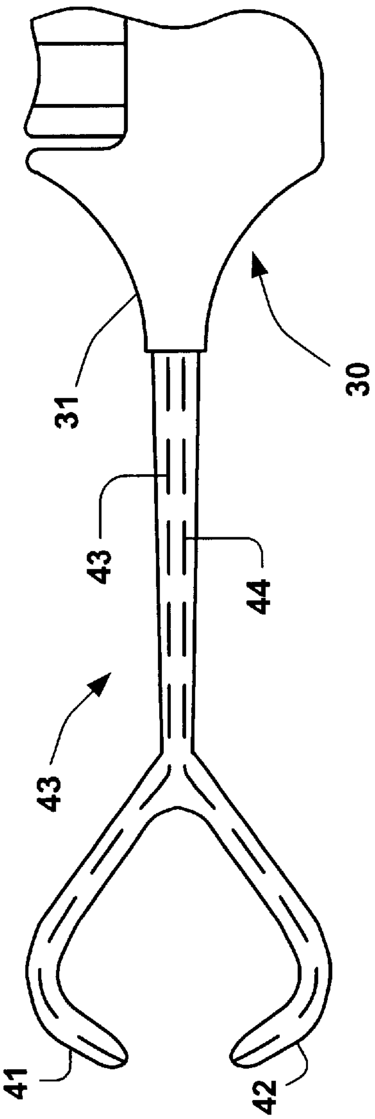
FIG. 4 is a view of a dual irrigator attachment for the cleaning device.

FIG. 4 illustrates a dual-irrigator attachment 40 having a discharge orifice 42 and a conduit 44 (indicated by a dashed line) that places the discharge orifice 42 in fluid communication with the first conduit 16 of the pump 10. The dual-irrigator attachment 40 also has a vacuum suction orifice 41 and a conduit 43 (indicated by a dashed line) that places the suction orifice 41 in fluid communication with the third conduit 24 of the pump 10.

FIGS. 5*a* and 5*b* illustrate the dual-irrigator attachment 40 positioned to clean two teeth 51 and 52. An adjustable high-pressure fluid discharged from the discharge orifice 42 alone would remove some particles that are between the teeth. However, with the aid of the suction action at the suction orifice 41, the fluid becomes more active and more particles are removed. The ravaging action combined with the suction action provides a much improved irrigator. Maximum cleaning capability can be obtained by adjusting the discharge volume and pressure to maximum.

Figure 6:
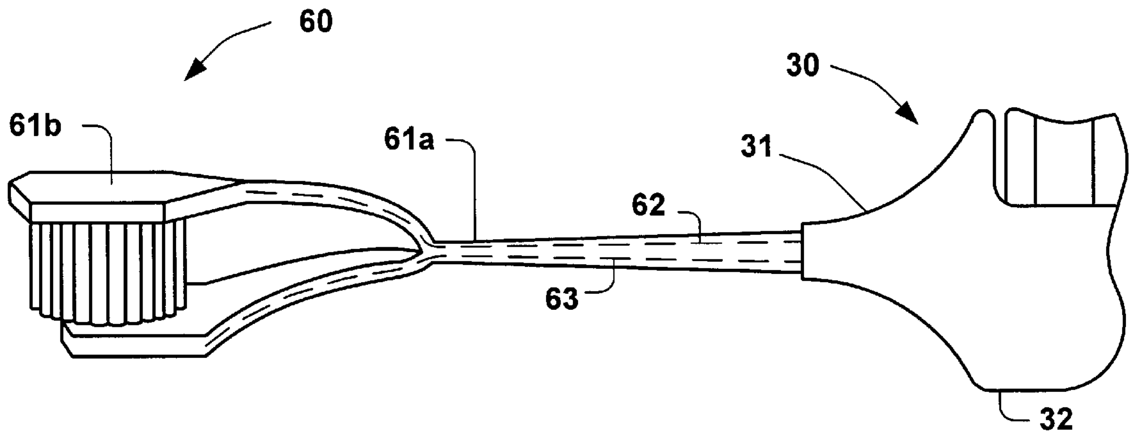
FIG. 6 is a view of a multi-head toothbrush attachment for the cleaning device.
Figure 7:
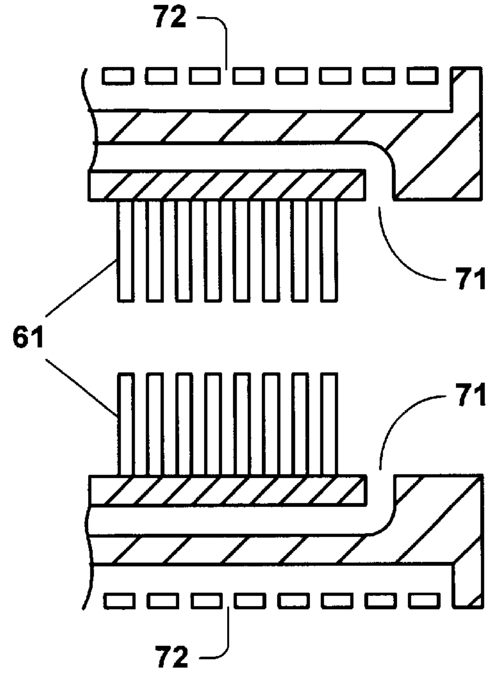
FIG. 7 is a sectional view of a brush head for the multi-head toothbrush, the view showing fluid passages for lavaging and suction operations.

FIGS. 6 and 7 illustrate a multi-head toothbrush 60 that can be attached to the discharge section 31. First and second flow passages 62 and 63 (indicated by dashed lines) in the toothbrush body 61*a* and heads 61*b* allow water or therapeutic fluid to be injected into and removed from a user's mouth. The fluid aids in cleaning the teeth. The fluid is injected into the user's mouth via a first orifice 71, which is in fluid communication with the first conduit 16 via the first flow passage 62. The fluid in the user's mouth is withdrawn through a second orifice 72, which is in fluid communication with the third conduit 24 via the second flow passage 63. The waste fluid is pumped to the fourth conduit 23 and can be disposed conveniently to a sink. The multi-head toothbrush 60 is more efficient in cleaning the teeth than a single brush. The combination of the lavaging and suction capabilities results in a more efficient cleaning device.

Figure 8:
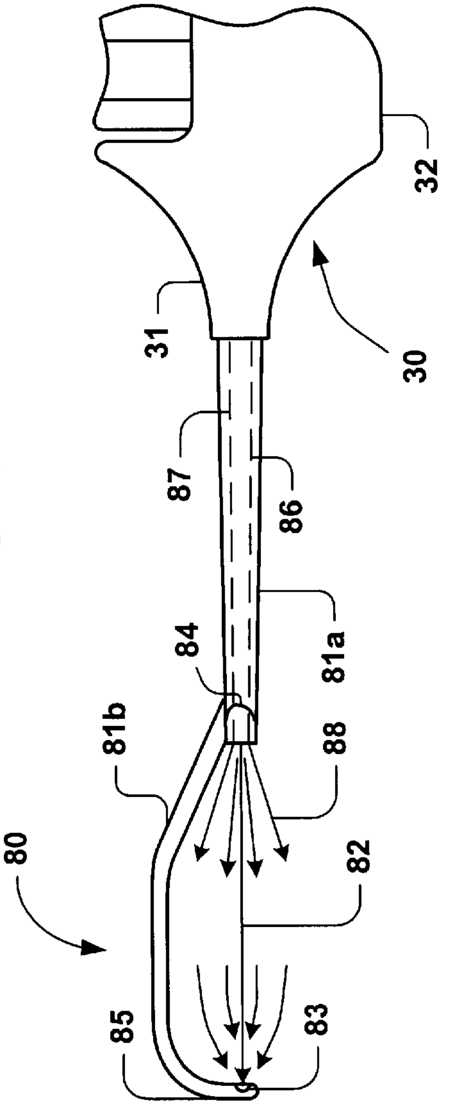
FIG. 8 is a view of a flossing attachment for the cleaning device.

FIG. 8 illustrates a flossing attachment 80 for the cleaning device 30. The flossing attachment 80 includes a body 81*a* that terminates in a bridge 81*b*. Dental floss 82 is held in place by hooks 84 and 85. First and second conduits 86 and 87 (indicated by dashed lines) extend though the body 81*a*. Fluid from the reservoir 18 is pumped through the first conduit 16 of the pump 10 and through the first conduit 86 of the attachment body 81*a* to a discharge port 88, which sprays fluid onto the dental floss 82 and into the user's mouth. Cleaning is improved by the suction action that draws waste fluid and debris through the space between the teeth and into suction ports 83. From the suction ports 83 the waste fluid and debris travel through the second conduit 87 of the attachment body 81*a*, through the third conduit 24 of the pump 10 and into the second chamber 19. The waste fluid and debris may be disposed to a sink via the fourth conduit 23.

Figure 10:
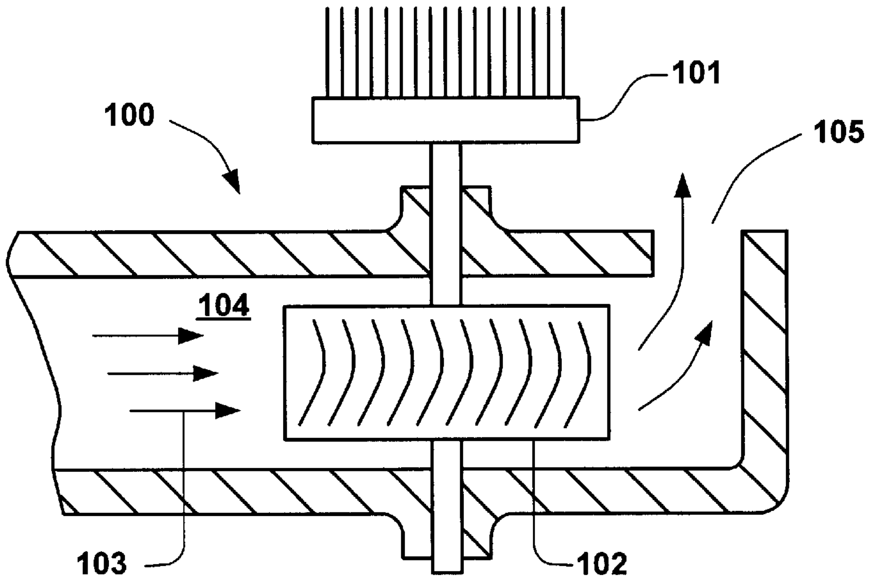
FIG. 10 is a view of a rotating toothbrush attachment for the cleaning device.

FIG. 10 illustrates an attachment 100 including a small toothbrush 101 that is mechanically connected to a turbine 102 and mounted transversely in a conduit 104. The pump 10 discharges cleaning fluid 103 through its first conduit 16 and into the attachment conduit 104, whereby the fluid 103 causes the turbine 102 to rotate the small toothbrush 101. The cleaning fluid 103 continues past the turbine 102 and enters the user's mouth through a port 105. The attachment 100 also has a suction port (not shown) in fluid communication with the third conduit 24.

FIGS. 11*a* and 11*b* illustrate an eye wash attachment 111 for the cleaning device 30. The eye wash attachment 111 may be used for removing contaminants from a person's eye. The eye wash attachment 111 includes an eyecup 113 having multiple orifices 115 and a tube 112 that places the orifices 115 in fluid communication with the first conduit 16 of the pump 10. During use, the eyecup 113 is placed over a person's eye, and the finger grip 13 is depressed. Cleaning fluid is ejected from the first conduit 16, into the attachment tube 112, through the orifices 115, and into the eye ocular cul-de-sac to remove the contaminant. This eye wash attachment 111 is particularly useful in factories where eyewash fountains are not available. The eye wash attachment 111 may be provided with a control valve 114 for regulating the pressure that is delivered to the multiple offices 115, even though the pressure may be regulated by the first valve 15 of the pump 10.

Figure 12B:
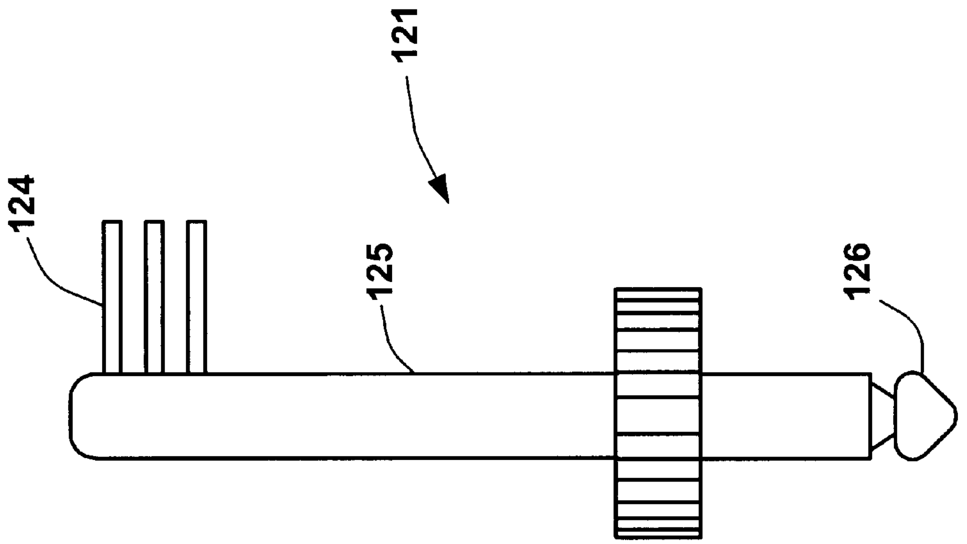
FIGS. 12*a* and 12*b* are illustrations of a tongue scraping attachment for the cleaning device.
Figure 12A:
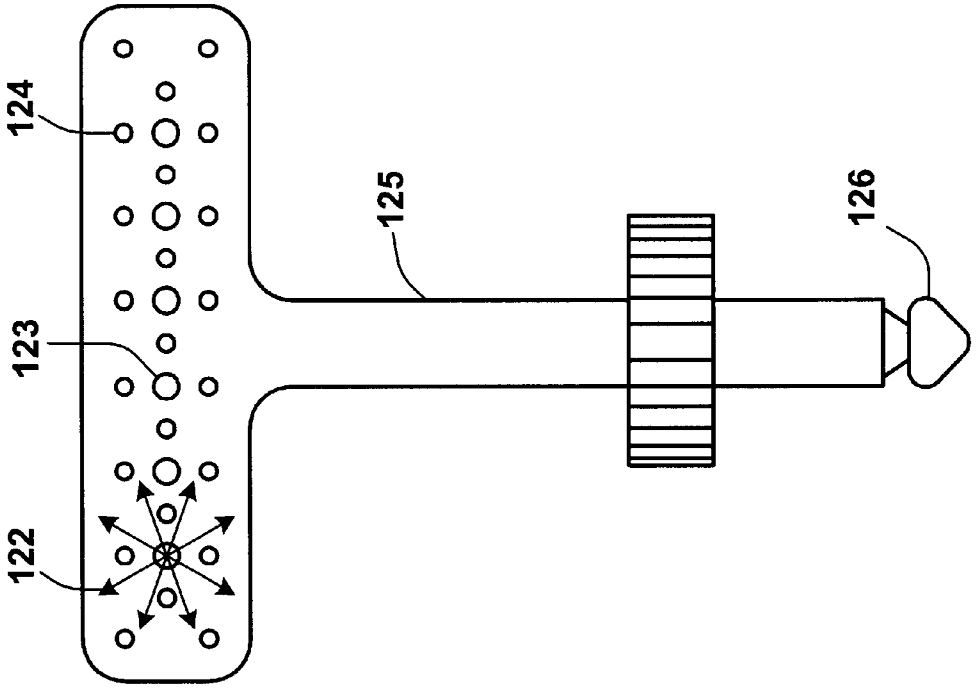

FIGS. 12*a* and 12*b* illustrate a tongue cleaning attachment 121 including a body 125, and soft plastic tips 124 for removing deposits. A conduit (not shown) in the body 125 allows the cleaning device 30 to dispense fluid 122 through orifices 123 to aid the soft plastic tips 124 in removing any deposits. The tongue cleaning attachment 121 also has a suction port (not shown) in fluid communication with the third conduit 24. Deposits and fluid are removed via the suction port. Cleaning the tongue each time a person brushes his or her teeth may be performed to maintain a healthy oral cavity. The body 125 of the tongue cleaning attachment 121 terminates in a connector head 126. The connector head 126 snaps into the discharge section 31.

Figure 13:
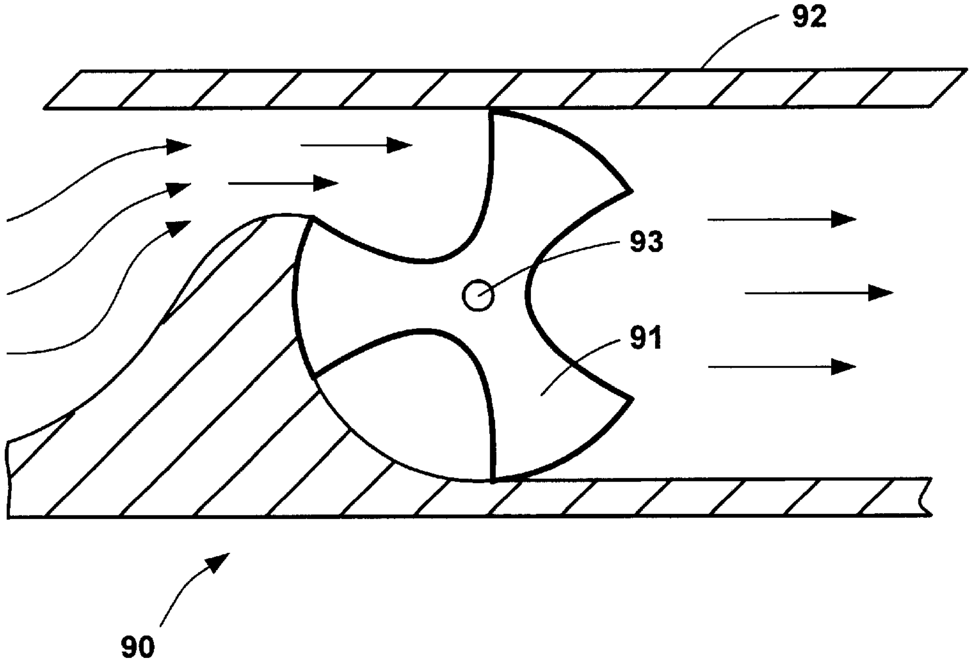
FIG. 13 is a view of a stream-pulsing attachment for the cleaning device.

FIG. 13 illustrates an attachment 90 for providing a pulsating stream, which improves the lavaging capability. The pulsating stream can be created by a wheel 91 having vanes. The wheel 91 is supported within a conduit 92 by a pin 93 that is transverse to the conduit 92. The fluid discharged from the first conduit 16 of the pump 10 causes the wheel 91 to rotate, resulting in a pulsing stream of fluid. This pulsing stream attachment 90 may be used in combination with any of the attachments described above. For example, the pulsating stream attachment 90 may be located between the discharge section 31 and the dual-irrigator attachment 40.

The cleaning attachments may be connected to the discharge section 31 in a variety of ways. FIGS. 12*a* and 12*b* show but one example.

Thus disclosed is a cleaning device that provides lavaging and suction action. The lavaging action combined with the suction action provides a much improved cleaning capability.

The device attachments allow a wide variety of cleaning operations. The discharge volume and pressure can be adjusted to suitable levels for different operations. For example, the discharge pressure for the eye wash attachment would be lower than the discharge pressure for the oral irrigation attachment.

The device is not limited to the cleaning operations described above. Other cleaning operations could be provided by other attachments.

Non-detachable cleaning devices could be formed integrally with the discharge section of the cleaning device. For example, a multi-head toothbrush could be formed integrally with the discharge section of the cleaning device.

The invention is not limited to the specific embodiments described and illustrated above. Instead, the present invention is construed according to the claims that follow.

What is claimed is:

1. A handheld cleaning device comprising:

a cleaning section having a discharge port and a suction port, the cleaning section further having a dual head irrigator with ports that are in fluid communication with the suction and discharge ports; and a pump for creating fluid discharge pressure at the discharge port of the cleaning section and for simultaneously creating suction at the suction port of the cleaning section.

2. The device of claim 1, further comprising a fluid reservoir section, the pump intermediate the cleaning and reservoir sections, the pump causing fluid in the reservoir section to be discharged through the discharge port of the cleaning section.

3. The device of claim 1, wherein the pump includes:

a cylinder;

a piston movable within the cylinder, one side of the piston defining a first chamber, an opposite side of the piston defining a second chamber;

a first conduit extending between the first chamber and the discharge port of the cleaning section; and a second conduit extending from the second chamber to the suction port of the cleaning section;

fluid being forced out of the first chamber and fluid being drawn into the second chamber simultaneously when the piston is moved in a first direction.

4. A handheld cleaning device comprising:

a cleaning section having a discharge port and a suction port, the cleaning section further having a toothbrush with ports that are in fluid communication with the suction and discharge ports; and a pump for creating fluid discharge pressure at the discharge port of the cleaning section and for simultaneously creating suction at the suction port of the cleaning section.

5. The device of claim 4, further comprising a fluid reservoir section, the pump intermediate the cleaning and reservoir sections, the pump causing fluid in the reservoir section to be discharged through the discharge port of the cleaning section.

6. The device of claim 4, wherein the pump includes:

a cylinder;

a piston movable within the cylinder, one side of the piston defining a first chamber, an opposite side of the piston defining a second chamber;

a first conduit extending between the first chamber and the discharge port of the cleaning section; and a second conduit extending from the second chamber to the suction port of the cleaning section;

fluid being forced out of the first chamber and fluid being drawn into the second chamber simultaneously when the piston is moved in a first direction.

7. A handheld cleaning device comprising:

a cleaning section having a discharge port and a suction port, the cleaning section further having a dental flossing device with ports that are in fluid communication with the suction and discharge ports; and a pump for creating fluid discharge pressure at the discharge port of the cleaning section and for simultaneously creating suction at the suction port of the cleaning section.

8. The device of claim 7, further comprising a fluid reservoir section, the pump intermediate the cleaning and reservoir sections, the pump causing fluid in the reservoir section to be discharged through the discharge port of the cleaning section.

9. The device of claim 7, wherein the pump includes:

a cylinder;

a piston movable within the cylinder, one side of the piston defining a first chamber, an opposite side of the piston defining a second chamber;

a first conduit extending between the first chamber and the discharge port of the cleaning section; and a second conduit extending from the second chamber to the suction port of the cleaning section;

fluid being forced out of the first chamber and fluid being drawn into the second chamber simultaneously when the piston is moved in a first direction.

10. A handheld cleaning device comprising:

a cleaning section having a discharge port, a suction port, and a vane wheel for creating a pulsing stream from fluid discharge at the discharge port; and a pump for creating fluid discharge pressure at the discharge of the cleaning section and for simultaneously creating suction at the suction of the cleaning section.

11. The device of claim 10, further comprising a fluid reservoir section, the pump intermediate the cleaning and reservoir sections, the pump causing fluid in the reservoir section to be discharged through the discharge port of the cleaning section.

12. The device of claim 10, wherein the pump includes:

a cylinder, a piston movable within the cylinder, one side of the piston defining a first chamber, an opposite side of the piston defining a second chamber;

a first conduit extending between the first chamber and the discharge port of the cleaning section; and a second conduit extending from the second chamber to the suction port of the cleaning section;

fluid being forced out of the first chamber and fluid being drawn into the second chamber simultaneously when the piston is moved in a first direction.

13. A handheld cleaning device comprising:

a cleaning section having a discharge port, a suction port, and an eye wash device; and a pump for creating fluid discharge pressure at the discharge port of the cleaning section and for simultaneously creating suction at the suction port of the cleaning section.

14. The device of claim 13, further comprising a fluid reservoir section, the pump intermediate the cleaning and reservoir sections, the pump causing fluid in the reservoir section to be discharged through the discharge port of the cleaning section.

15. The device of claim 13, wherein the pump includes:

a cylinder;

a piston movable within the cylinder, one side of the piston defining a first chamber, an opposite side of the piston defining a second chamber;

a first conduit extending between the first chamber and the discharge port of the cleaning section; and a second conduit extending from the second chamber to the suction port of the cleaning section;

fluid being forced out of the first chamber and fluid being drawn into the second chamber simultaneously when the piston is moved in a first direction.

16. A handheld cleaning device comprising:

a cleaning section having a discharge port, a suction port, and a tongue scraper; and a pump for creating fluid discharge pressure at the discharge port of the cleaning section and for simultaneously creating suction at the suction port of the cleaning section.

17. The device of claim 16, further comprising a fluid reservoir section, the pump intermediate the tongue cleaning and reservoir sections, the pump causing fluid in the reservoir section to be discharged through the discharge port of the cleaning section.

18. The device of claim 16, wherein the pump includes:

a cylinder;

a piston movable within the cylinder, one side of the piston defining a first chamber, an opposite side of the piston defining a second chamber;

a first conduit extending between the first chamber and the discharge port of the cleaning section; and a second conduit extending from the second chamber to the suction port of the cleaning section;

fluid being forced out of the first chamber and fluid being drawn into the second chamber simultaneously when the piston is moved in a first direction.

* * * * *